United States Patent [19]

Terao et al.

[11] Patent Number: 4,751,303
[45] Date of Patent: Jun. 14, 1988

[54] BENZOQUINONE DERIVATIVES AND PRODUCTION THEREOF

[75] Inventors: Shinji Terao, Toyonaka; Hisayoshi Okazaki, Kyoto; Isuke Imada, Izumi, all of Japan

[73] Assignee: Takeda Chemical Industries, Ltd., Osaka, Japan

[21] Appl. No.: 717,098

[22] Filed: Mar. 28, 1985

Related U.S. Application Data

[62] Division of Ser. No. 484,232, Apr. 11, 1983, Pat. No. 4,526,719.

[30] Foreign Application Priority Data

Apr. 13, 1982 [JP] Japan .................. 57-62224

[51] Int. Cl.$^4$ ............... C07D 265/30; C07D 265/32
[52] U.S. Cl. ................................ 544/173; 544/174
[58] Field of Search ..................... 544/173, 174

[56] References Cited

U.S. PATENT DOCUMENTS

| | | | |
|---|---|---|---|
| 4,271,083 | 6/1981 | Morimoto et al. | 260/396 R |
| 4,608,435 | 8/1986 | Howell | 544/173 |

FOREIGN PATENT DOCUMENTS

| | | | |
|---|---|---|---|
| 0021841 | 1/1981 | European Pat. Off. | 260/396 R |
| 0025692 | 3/1981 | European Pat. Off. | 260/396 R |
| 0031727 | 7/1981 | European Pat. Off. | 260/396 R |
| 0038160 | 10/1981 | European Pat. Off. | 260/396 R |
| 0038674 | 10/1981 | European Pat. Off. | 260/396 R |
| 0058057 | 8/1982 | European Pat. Off. | 260/396 R |
| 1252194 | 10/1967 | Fed. Rep. of Germany | 260/396 R |
| 2269333 | 11/1975 | France | 260/396 R |
| 819654 | 9/1959 | United Kingdom | 260/396 R |

*Primary Examiner*—Richard L. Raymond
*Assistant Examiner*—Raymond Covington
*Attorney, Agent, or Firm*—Wenderoth, Lind & Ponack

[57] ABSTRACT

A novel benzoquinone derivative of the general formula:

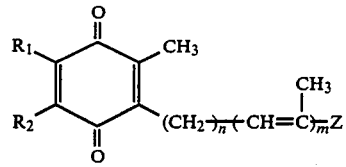

[wherein $R_1$ and $R_2$ are the same or different and each is methyl or methoxy; n is an integer of 0 to 21; m is 0 or 1, Z is a group of the formula:

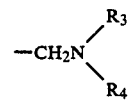

(wherein $R_3$ and $R_4$ are the same or different and each is hydrogen or an alkyl group which may optionally be substituted or, $R_3$ and $R_4$ together with the adjacent nitrogen atom form a morpholino group), a group of the formula: —$COR_5$ (wherein $R_5$ is an α-amino acid residue or a substituted or unsubstituted glucosamine residue), a group of the formula:

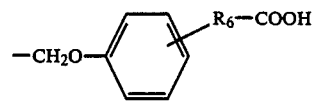

(wherein $R_6$ is a divalent hydrocarbon group of 1 to 3 carbon atoms), a group of the formula:

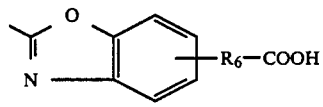

(wherein $R_6$ has the same meaning as defined above) or a group of the formula: —CH=CH)$_l$COR$_7$ (wherein l is an integer of 1 to 4 and $R_7$ is hydroxy, methoxy or methyl)] has protocollagen-proline hydroxylase inhibiting activity, collagen biosynthesis inhibiting activity and 5-lipoxygenase suppressant activity, and is useful for the prevention and treatment of such diseases as pulmonary fibrosis, hepatocirrhosis, nephrosclerosis, arteriosclerosis, scleroderma, myelofibrosis and chronic arthritis or for the prevention and treatment of asthma, allergic rhinitis, urticaria, etc.

6 Claims, No Drawings

BENZOQUINONE DERIVATIVES AND PRODUCTION THEREOF

This application is a division of application Ser. No. 484,232, filed Apr. 12, 1983 (now U.S. Pat. No. 4,526,719).

This invention relates to novel benzoquinone derivatives having inhibitory activities of protocollagen-proline hydroxylase, collagen biosynthesis and 5-lipoxygenase.

Protocollagen proline hydroxylase is an enzyme which specifically hydroxylates the proline residues of the protocollagen synthesized by ribosomes in animal cells and is one of the important rate-determinant factors in collagen biosynthesis. Heretofore-known inhibitors of this enzyme activity include ferrous or ferric chelating agents (e.g. α,α'-dipyridyl, etc.). SH enzyme inhibitors (e.g. p-chloromercury benzoate, etc.) and certain heavy metals (e.g. $Cu^{++}$, $Zn^{++}$, etc.). However, since these substances entail major side effects as they invariably cause a nonspecific inhibition of biosynthesis of collagen and non-collagen proteins, none of them could be used as a pharmaceutical product. It follows, therefore, that development of a substance that will specifically inhibit collagen biosynthesis without inhibiting the biosynthesis of other non-collagen proteins at all, the substance would be useful for the prevention and treatment of organ fibrosis and other diseases which may be caused by an excessive accumulation of collagen such as arteriosclerosis, hepatocirrhosis, scleroderma, keloid, rheumatoid arthritis and pulmonary fibrosis.

The present inventors explored the possibility of developing a substance that may inhibit protocollagen proline hydroxylase activity and found that such an inhibitory activity resides in novel benzoquinone derivatives which are represented by the general formula

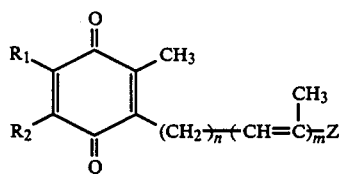

(I)

[wherein $R_1$ and $R_2$ are the same or different and each is methyl or methoxy; n is an integer of 0 to 21; m is 0 or 1, Z is a group of the formula:

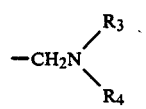

(wherein $R_3$ and $R_4$ are the same or different and each is hydrogen or an alkyl group which may optionally be substituted or, $R_3$ and $R_4$ together with the adjacent nitrogen atom form a morpholino group), a group of the formula: $-COR_5$ (wherein $R_5$ is an α-amino acid residue or a substituted or unsubstituted glucosamine residue), a group of the formula:

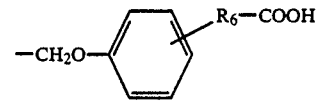

(wherein $R_6$ is a divalent hydrocarbon group of 1 to 3 carbon atoms), a group of the formula:

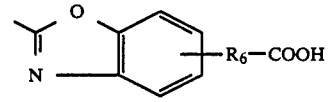

(wherein $R_6$ has the same meaning as defined above) or a group of the formula: $-CH=CH)_lCOR_7$ (wherein l is an integer of 1 to 4 and $R_7$ is hydroxy, methoxy or methyl)]. It was also found that these compounds suppress production of slow reacting substance of anaphylaxis (hereafter briefly, SRS-A) as well. These findings have resulted in the present invention.

This invention is therefore directed to benzoquinone derivatives of general formula (I).

In the above general formula (I), the alkyl group which may optionally be substituted as designated by $R_3$, $R_4$ in the group

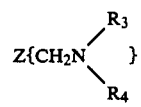

is a $C_{1-4}$ alkyl group (e.g. methyl, ethyl, propyl) which may be substituted by halogen (Cl, Br, etc.), nitro, amino, hydroxy, etc. The α-amino acid residue $R_5$ in the group $Z\{COR_5\}$ is the one which has 2 to 11 carbon atoms and is obtainable by removal of one hydrogen atom from the α-amino group of an α-amino acid which is exemplified by glycine, alanine, proline, phenylalanine, glutamic acid, methionine, tyrosine, arginine, thioproline, tryptophan, lysine, valine, histidine, leucine, isoleucine, serine, threnonine, cysteine, aspartic acid, oxyproline, etc. The glucosamine residue which may optionally be substituted as designated by $R_5$ is a group obtainable after removal of one hydrogen atom from either the amino group or the hydroxy group of glucosamine, and the substituent may for example be 1-carboxyethyl and may be present in any optional substitutable position of glucosamine. The hydrocarbon residue of 1 to 3 carbon atoms as designated by $R_6$ in the group

may for example be alkylenes (e.g. methylene, ethylene, propylene etc.), alkenylenes (vinylene, allylene), etc.

The pharmacological actions of compounds (I) according to this invention are described hereinafter.

(1) Inhibitory activity of protocollagen-proline hydroxylase

Determination of this inhibitory activity was made by the method of R. E. Rhoads et al. [Methods in Enzymology XVII B, 306 (1971)] using a partially purified enzyme preparation obtained from chick embryos in accordance with the methods of K. I. Kivirriko et al. and J. Halme et al. [J. Biol, Chem. 242, 4007 (1967) and Biochim. Biophys. Acta 198, 460 (1967)] and, as a substrate, (Pro-Pro-Gly)$_5$.4H$_2$O [prepared by the Protein Research Foundation, Osaka]. In this procedure, the partially purified enzyme was used in an amount of 100 μg as protein.

TABLE 1

Compound (I')

structure: 2,3-dimethoxy-5-methyl-1,4-benzoquinone with side chain $(CH_2)_n(CH=C(CH_3))_m Z$

| Compound (I') | Concentration (μM) | Inhibition (%) |
|---|---|---|
| m:0, n:2, Z:CO—Gly | 20 | 46 |
| m:0, n:2, Z:CO—Pro | 20 | 35 |
| m:0, n:2, Z:CO—Ala | 20 | 32 |
| m:0, n:9, Z:CO—Phe | 20 | 35 |
| m:0, n:9, Z:CO—Glu | 20 | 37 |
| m:0, n:9, Z:CO—MurNAc | 20 | 32 |
| m:0, n:9, Z:CO—GlcN | 20 | 52 |
| m:0, n:2, Z:CO—Glu | 20 | 20 |
| m:0, n:2, Z:CO abm4 Tyr | 20 | 35 |
| m:0, n:2, Z:CO—Arg (salt of acetic acid) | 20 | 56 |
| m:0, n:9, Z:CO—N[thiazolidine-COOH] | 20 | 35 |
| m:0, n:9, Z:CO—Arg (salt of acetic acid) | 20 | 52 |
| m:0, n:9, Z:CO—Met | 20 | 38 |
| m:0, n:9, Z:CO—Trp | 20 | 15 |
| m:0, n:9, Z:CO—Lys | 20 | 25 |
| m:0, n:9, Z:CO—His | 20 | 52 |
| m:0, n:0, Z:CH$_2$—morpholino | 20 | 78 |
| m:0, n:9, Z:CH$_2$—morpholino (salt of hydrochloric acid) | 25 | 30 |
| m:0, n:3, Z:CH$_2$N(CH$_3$)$_2$ (salt of oxalic acid) | 25 | 70 |
| m:0, n:0, Z:CH$_2$N(CH$_3$)$_2$ (salt of hydrochloric acid) | 20 | 82 |
| m:0, n:3, Z:CH$_2$—O—C$_6$H$_4$—CH=CH—COOH | 50 | 94 |
| | 20 | 55 |
| | 10 | 39 |

TABLE 1-continued

Compound (I')

| Compound (I') | Concentration (μM) | Inhibition (%) |
|---|---|---|
| m:1, n:1, Z:CH$_2$—O—C$_6$H$_4$—CH=CH—COOH | 50 | 83 |
| | 20 | 52 |
| | 10 | 43 |
| m:0, n:1, Z:CH$_2$—O—C$_6$H$_4$—CH=CH—COOH | 50 | 100 |
| | 20 | 100 |
| | 10 | 99, 94 |
| | 5 | 72 |
| | 2.5 | 62 |
| m:1, n:1, Z:CH$_2$—O—C$_6$H$_4$—CH$_2$—COOH | 50 | 92 |
| | 20 | 48 |
| | 10 | 34 |
| m:0, n:1, Z:CH$_2$—O—C$_6$H$_4$—CH$_2$—COOH | 50 | 100 |
| | 20 | 100 |
| | 10 | 100, 82 |
| | 5 | 74 |
| | 2.5 | 64 |
| m:0, n:0, Z:CH$_2$—O—C$_6$H$_4$—CH(CH$_3$)—COOH | 50 | 100 |
| | 20 | 100 |
| | 10 | 100, 92 |
| | 5 | 75 |
| | 2.5 | 70 |
| m:0, n:0, Z: CH=CH—CH=CH—CH=CH—COOCH$_3$ | 50 | 76 |
| | 20 | 67 |
| | 10 | 38 |
| m:0, n:0, Z: benzoxazole-phenyl-CH(CH$_3$)COOH | 50 | 84 |
| | 20 | 76 |
| | 10 | 54 |
| m:0, n:0, Z: CH=CH—COOH | 50 | 68 |
| | 20 | 46 |
| | 10 | 37 |
| | 5 | 22 |
| | 2.5 | 0 |
| m:0, n:0, Z: CH=CH—COCH$_3$ | 50 | 92 |
| | 20 | 92 |
| | 10 | 85 |
| | 5 | 72 |
| | 2.5 | 51 |

Where
Gly: glycyl
Ala: alanyl
Glu: glutamyl
Arg: arginyl
Lys: lysyl
Met: methionyl
GlcN: glucosamine residue

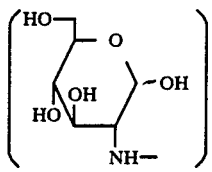

Pro: prolyl
Phe: phenylalanyl
Thr: tyrosyl
His: histidyl
MurNAc: N-acetyl muramic acid residue

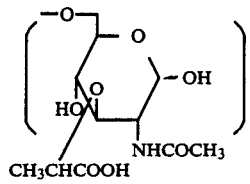

(2) Inhibitory activity of collagen biosynthesis

In accordance with the method of R. A. Salvador et al. [Arch. Biochem. Biophys. 174, 382 (1976)], 0.2 mg/kg of each test compound was intraperitoneally administered to SD strain rats (♀, 3 weeks old) once a day for 6 days. After that, the collagen content of the uterus was determined and compared with that of control experiment.

then, a test solution (0.5 ml of MCM, 50 μg of arachidonic acid, 10 μg of A-23187 and 1 μM or 10 μM of the quinone compound) is added. The reaction is conducted at 37° C. for 20 minutes. After completion of the reaction, 4 ml of ethanol including 1,4-dimethoxy-2-methyl-3-(3-methoxypropyl)naphthalene are added (0.5 μg/ml) are added as an internal reference. After shaking well, the mixture is allowed to stand at room temperature for 10 minutes. Then, the mixture was centrifuged (2000 r.p.m./min.) for 10 minutes and the supernatant is separated. This supernatant is concentrated under reduced pressure to about 200 μl. To the concentrate is added a high performance liquid chromatography solvent [CH$_3$CN(1500):CH$_3$OH(500):water (1100):acetic acid(2); pH 5.6 (adjusted with aqueous ammonia)] to make a total of 1 ml. A 200 μl portion of this solution is taken and 5-HETE (5-hydroxyeicosatetraenoic acid) is assayed by high performance liquid chromatography. The degree of inhibition of 5-HETE production (IE) is expressed in terms of $$\left(1 - \frac{b}{a}\right) \times 100,$$

where a is the peak height or area after correction with the peak of the internal reference standard in the absence of the quinone compound and b is the peak height or area after correction with the peak of the internal reference standard in the presence of the quinone compound.

TABLE 2

Test compound (I″)

| | | Body weight of rats* (g) | Collagen content of uterus (mg) | Degree of inhibition** (%) |
|---|---|---|---|---|
| (A) | Control | 73 ± 6 | 1.64 ± 0.3 | — |
| (B) | 17β-estradiol | 73 ± 3 | 3.45 ± 0.11 | — |
| (C) | 17β-estradiol + Compound of formula (I″) (n: 9, Z: CONH—Arg) | 71 ± 5 | 2.86 ± 0.75 | 33 |
| | 17β-estradiol + Compound of formula (I″) (n: 0, Z: ⟋⟍COOH) | 68 ± 3 | 2.53 ± 0.28 | 51 |
| | 17β-estradiol + Compound of formula (I″) (n: 0, Z: ⟋⟍COCH$_3$) | 69 ± 6 | 2.98 ± 0.15 | 26 |
| | 17β-estradiol + Compound of formula (I″) (N: 0, Z: CH$_2$O—C$_6$H$_4$—CH=CH—COOH) | 67 ± 3 | 2.77 ± 0.25 | 38 |

*Rats were used 3 animals as one group; initial body weights 41 ± 2 − 42 ± 4 g.
**Degree of inhibition (%) = $\frac{(B) - (C)}{(B) - (A)} \times 100$ (3) Inhibition of 5-lipoxygenase activity in RBL-1 cells 10$^7$ RBL-1 cells (rat basophilic leukemia cells) are suspended in 0.5 ml of MCM (mast cell medium), and,

TABLE 3

Test compound (I''')

$R_1$, $R_2$ quinone with CH$_3$ and $(CH_2)_n(CH=C(CH_3))_m Z$ substituents

| Test compound | Inhibition of 5-HETE production (%) Concentration of test compound | |
|---|---|---|
| | 1 μM | 10 μM |
| $R_1$: CH$_3$O, $R_2$: CH$_3$O, m: 0, n: 3, Z: CH$_2$—O—C$_6$H$_4$—CH=CH—COOH | 72.0 | 83.1 |
| $R_1$: CH$_3$O, $R_2$: CH$_3$O, m: 1, n: 1, Z: CH$_2$—O—C$_6$H$_4$—CH=CH—COOH | 76.6 | 85.8 |
| $R_1$: CH$_3$O, $R_2$: CH$_3$O, m: 0, n: 0, Z: CH$_2$—O—C$_6$H$_4$—CH=CH—COOH | 73.9 | 83.5 |
| $R_1$: CH$_3$O, $R_2$: CH$_3$O, m: 1, n: 1, Z: CH$_2$—O—C$_6$H$_4$—CH$_2$—COOH | 72.2 | 83.3 |
| $R_1$: CH$_3$O, $R_2$: CH$_3$, m: 0, n: 0, Z: CH$_2$—O—C$_6$H$_4$—CH$_2$—COOH | 70.1 | 81.5 |
| $R_1$: CH$_3$, $R_2$: CH$_3$, m: 0, n: 0, Z: phthalimido-CH(CH$_3$)—COOH | 63.5 | 79.2 |
| (control) (BW755C) CF$_3$-phenyl-pyrazoline-NH$_2$ | 21.8 | 39.1 |
| (control) ETYA* | 35.9 | 39.4 |

*ETYA: Eicosatetraynoic acid

As mentioned hereinbefore, compounds (I) of this invention have inhibitory activities of protocollagen-proline hydroxylase collagen biosynthesis and 5-lipoxygenase. The present compound is low in toxicity, i.e. its LD$_{50}$ value in rat is more than 500 mg/kg (P.O.). Therefore, these compounds are useful as drugs for the prevention and treatment of organ fibrosis in mammalian animals (e.g. rabbit, rat, mouse, dog, cat, human), for the prevention and treatment of such diseases as plumonary fibrosis, hepatocirrhosis, nephrosclerosis, arteriosclerosis, scleroderma, myelofibrosis and chronic arthritis or as antiallergic drugs in the prevention and treatment of asthma, allergic rhinitis, urticaria, etc.

The compounds (I) of this invention may each be administered orally or otherwise, either as it is or as formulated with appropriate pharmacologically acceptable carriers, excipients or/and diluents, in various dosage forms such as powders, granules, tablets, capsules, injections, etc. The dosage depends on the kinds of disease, symptoms, subject, route of administration, or dosage forms, but in case of parenteral administration such as injection, the daily dose as the compound (I) is about 25 mg to 500 mg (0.5 mg to 10 mg/kg), preferably 50 mg to 250 mg (1.0 mg to 5 mg/kg) for adult human, and in case of oral administration, the daily dose is about 100 mg to 1000 mg (1 mg to 10 mg/kg), preferably 250 mg to 500 mg (5 mg to 10 mg/kg) for adult human.

The composition of this invention contains a drug of dosage unit form. The drug of dosage unit form means a drug containing a daily dose of the compound (I) as described above, or its multiples (up to 4 times), or its measures (down to 1/40), which is in the physically separate unit form suitable for administering as a medicine. Each dosage unit generally contains 0.3 mg to 250 mg of the compound (I). Among them, an injection ampoule preferably contains 0.3 mg to 30 mg, and each of other forms preferably contains 10 mg to 250 mg of the compound (I).

The compounds of general formula (I) can be produced from a compound of general formula:

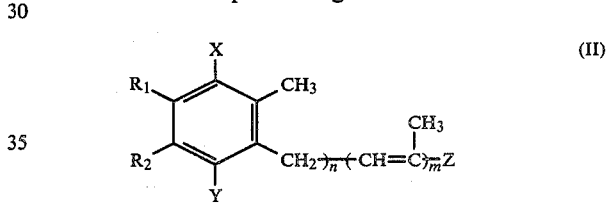

(II)

[wherein $R_1$, $R_2$, m, n and Z have the same meanings as defined hereinbefore; X is hydrogen or a hydroxy group which may optionally be protected; Y is a hydroxy group which may optionally be protected] by subjecting the compound (II) to oxidation reaction either directly or, as required, after elimination of the protective group(s).

Referring to the general formula (II), the protective group for hydroxy group X or Y may be any easily removable group, for example, an alkyl group of 1 to 4 carbon atoms such as methyl, ethyl, n-propyl, i-propyl, n-butyl, i-butyl, etc., an aralkyl group such as benzyl, etc., an acyl group such as acetyl, benzoyl, benzylcarbonyl, etc., an acetal group such as α-tetrahydropyranyl, methoxymethyl, etc. or a silyl group such as trimethylsilyl, etc. Among the protective group of hydroxyl shown by X and Y, aralkyl group can be removed by subjecting the compound (II) to hydrogenolysis in the presence of the catalyst such as palladium, palladium on carbon, platinum, etc., acyl group can be removed by subjecting the compound (II) to hydrolysis in the presence of a base such as potassium hydroxide, sodium hydroxide, potassium carbonate, sodium carbonate, etc., and acetal group and silyl group can be removed by subjecting the compound (II) to hydrolysis in the presence of an acid such as hydrochloric acid, sulfuric acid, toluenesulfonic acid, camphanesulfonic acid, etc. When the compound (II) wherein X or Y is hydroxyl protected by alkyl group is subjected to oxidative alkylation by using silver oxide or ammonium cerium (IV)

nitrate, the protective group is removed and the compound (II) is oxidized to give a compound (I).

The oxidation reaction may be any types of reactions that will transform phenol to quinone without affecting an alcoholic hydroxy group or deprotection reaction, and examples of the oxidizing agent include ferric chloride, silver oxide, nitrosodisulfonate, ammonium cerium (IV) nitrate, etc. The oxidizing agent is usually used in an amount of 1 to 3 moles per mole of compound (II).

This oxidation reaction is generally conducted in the presence of a suitable solvent. The solvent may be used if it is not susceptible to the oxidation reaction, thus being exemplified by water, a dilute acid or alkali solution, acetone, ethanol, dioxane, acetonitrile, ether, acetic acid, dimethylformamide, tetrahydrofuran, etc. The reaction temperature and the rate of this oxidation reaction depend on the oxidizing agent employed. This reaction is generally preferably conducted at −10 to +25° C. for 0.5 to 5 hours.

The compound (I) thus obtained can be isolated and purified by purification and separation procedure known per se such as concentration, concentration under reduced pressure, distillation, distillation under reduced pressure, fractional distillation, pH adjustment, solvent extraction, crystallization, recrystallization, phasic transfer and chromatography.

The compound of general formula (I) in which m is 0 and Z is a group of the formula: COR$_5$, that is a compound of general formula:

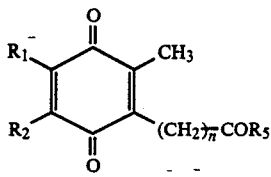
(I-a)

[wherein the symbols have the same meanings as defined hereinbefore], can also be produced by converting the carboxyl group of a compound of general formula:

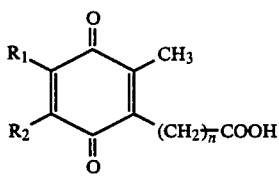
(III)

[wherein the symbols have the same meanings as defined hereinbefore] to a reactive derivative and, then, reacting the same with an α-amino acid which may optionally be protected or glucosamine which may optionally be substituted. The reactive derivative of carboxyl group may for example be an active ester or an acid anhydride. Examples of said active ester include the cyanomethyl ester, thioglycolic acid ester, p-nitrophenyl ester, 2,4,5-trichlorophenyl ester, pentachlorophenyl ester, pentafluorophenyl ester, pivalohydroxamic acid ester, N-hydroxyphthalimide ester, N-hydroxysuccinimide ester, N-hydroxy-5-norbornene-2,3-dicarboximide ester, 8-hydroxyquinolyl ester, 2-hydroxy-1,2-dihydro-1-carbethoxyquinolyl ester, 2-hydroxyphenyl ester, 2-hydroxy-4,5-dichlorophenyl ester, 2-hydroxypyridyl ester, 2-pyridylthiol ester, 1-hydroxybenzotriazol ester unsubstituted or substituted by halogenated methyl or methoxyl, and active esters such as enol esters which are obtainable with the use of N,N'-dicylohexylcarbodiimide or N-ethyl-5-phenyl-isoxazolium-3-sulfonate.

Preferred examples of said acid anhydride include mixed acid anhydrides and acid amides such as imidazolide, isoxazolide, etc.

When α-amino acid has a group or groups such as hydroxyl, guanyl, these groups may be protected. Further, when α-amino acid has two or more amino groups, the amino group(s) which is not allowed to react with a reactive derivative of compound (III) is usually protected. As a protective groups of the α-amino acid, the protective group which is conventionally used as a protective group in the field of peptide and glucose chemistry.

The substituents of the glucosamine include hydroxyl, amino, etc. These groups may be protected by alkyl (e.g. methyl, ethyl, propyl, etc.) or acyl (e.g. acetyl, etc.).

The reaction between a reactive derivative of compound (III) and an α-amino acid which may optionally be protected or glucosamine which may optionally be substituted may be conducted in the presence of an organic base, if necessary. In this reaction, about 0.8 to 1.2 mole of the α-amino acid is used per one mole of compound (III). Example of the base includes triethylamine, N-methylmorpholine, N-ethylmorpholine or 1-hydroxybenzotriazole, if necessary. The base is usually used in an amount of 1 to 2 moles per one mole of compound (III). The reaction is generally carried out at about 0° C. to about 80° C., and preferably about 5° to 50° C. for about one to two days. This reaction may be carried out at a temperature outside the above range, if desired. This reaction generally proceeds in a solvent, examples of which include ethers such as tetrahydrofuran, dioxane, etc., esters such as ethyl acetate, isoamyl acetate, etc., N-alkylamides such as N,N-dimethylformamide, N-methyl-2-pyrrolidone, N,N-dimethylacetamide, etc., and certain other solvents such as dimethyl sulfoxide, hexamethylphosphoramide, etc.

After completion of the above reaction, the protective group can be removed by a per se known procedure such as catalytic reduction with the aid of a metal catalyst or hydrolytic elimination with an acid.

The compound (I-a) thus obtained can be isolated and purified by purification and separation procedure known per se such as concentration, concentration under reduced pressure, distillation, distillation under reduced pressure, fractional distillation, pH adjustment, solvent extraction, crystallization, recrystallization, phasic transfer and chromatography.

The compound of general formula (II) in which Z is a group of the formula:

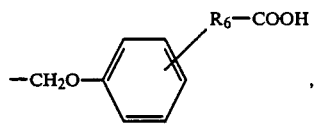

that is a compound of general formula:

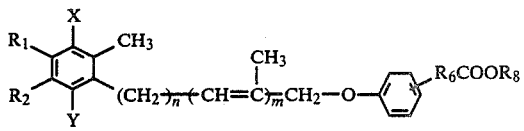

[wherein $R_8$ is hydrogen or a lower alkyl group; the other symbols have the same meanings as defined hereinbefore], can be produced by reacting a compound of general formula:

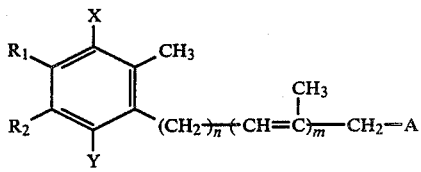

[wherein $R_1$, $R_2$, X, Y, n and m have the same meanings as defined hereinbefore; A is a halogen atom] with a compound of general formula:

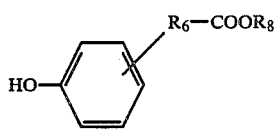

[wherein the symbols have the same meanings as defined hereinbefore] in the presence of a base. In the above compound (IV), the halogen atom A may for example be chlorine, bromine or iodine. The base may for example be sodium hydride or potassium tert-butoxide. The amount of base used in this reaction is usually about one to two moles per one mole of compound (IV). The amount of compound (V) to be contacted with compound (IV) is usually 0.8 to 1.2 mole per one mole of compound (IV). This reaction is usually carried out in the presence of a suitable solvent such as dimethylformamide, dimethylsulfoxide, tetrahydrofuran, etc. This reaction is usually carried out at about 0° C. to about 100° C. for 30 minutes to 3 hours.

The compound of general formula (II) in which Z is a group of the formula:

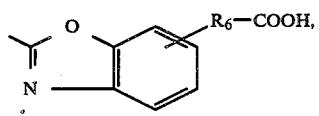

that is a compound of general formula:

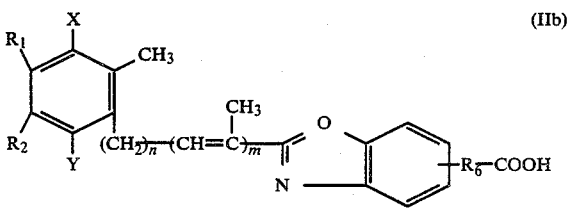

[wherein the symbols have the same meanings as defined hereinbefore], can be produced by subjecting a compound of general formula:

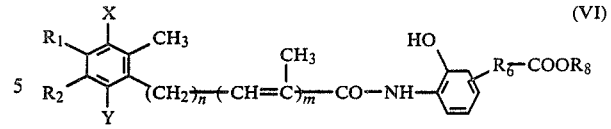

[wherein the symbols have the same meanings as defined hereinbefore] to dehydrative condensation. For this dehydrative condensation, phosphorous oxychloride or phosphorus pentachloride is preferably employed as dehydrating agent. The dehydrating agent is generally used in an amount of 2 to 5 mole per one mole of compound (VI). This reaction is carried out in the presence or absence of a solvent. Examples of the solvent include halogenated hydrocarbons (e.g. chloroform, dichloroethane, tetrachloroethane, etc.), aromatic hydrocarbons (e.g. benzene, toluene, xylene, etc.), etc. This reaction is usually carried out at about 60° to 150° C. for 1 to 5 hours.

The compound of general formula (II) in which Z is a group of the formula:

that is a compound of general formula:

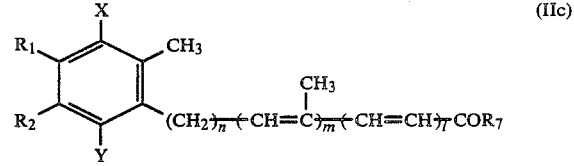

[wherein the symbols have the same meanings as defined hereinbefore], can be produced by subjecting an aldehyde compound of general formula:

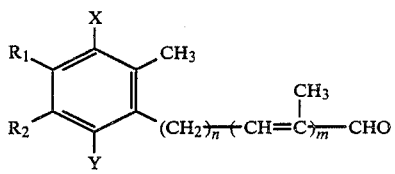

[wherein the symbols have the same meanings as defined hereinbefore], to Wittig reaction. That is, in this reaction, phosphonium salt is firstly reacted with a base to give a phosphorane and then the phosphorane is reacted to a compound (VII) to give a compound (IIc). Examples of the phosphonium salt include carboxymethylthriphenylphosphonium bromide, carboxymethyltriphenylphosphonium chloride, formylmethyltriphenylphosphonium chloride, etc. Examples of the base include sodium hydroxide, potassium hydroxide, potassium tert-butoxide, etc. The amount of the base is usually 1 to 1.5 mole per one mole of the phosphonium salt. In the second reaction, 1 to 1.5 mole of phosphorane is usually contacted with one mole of compound (VII). The Wittig reaction is usually carried out in the presence of a solvent such as diethyl ether, tetrahydrofuran, etc. The reaction temperature may range from 0° C. to the boiling point of the used solvent.

The compound of general formula (II) in which Z is a group of the formula:

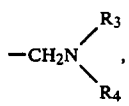

that is a compound of general formula:

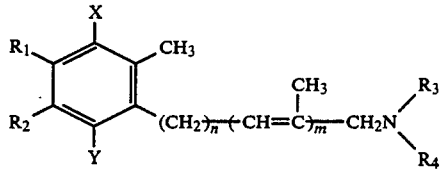
(IId)

[wherein the symbols have the same meanings as defined hereinbefore], can be produced by subjecting a compound of general formula (VII) and a compound of general formula:

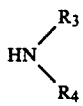
(VIII)

[wherein all the symbols have the meanings as defined hereinbefore] to Leuckart-Wallach reaction. That is, a compound of the formula (VII) is reacted with a compound of the formula (VIII) in the presence of formic acid to produce a compound of the formula (IId). This reaction is carried out in the absence or presence of a suitable solvent. Examples of the suitable solvent include alcohols such as methanol, ethanol, propanol, butanol, etc. The reaction temperature is usually 50° to 100° C., preferably 60° C. to 80° C. The reaction is usually 2 to 5 hours. In this reaction, about 0.8 to 1.2 mole of compound (VIII) is contacted with one mole of compound (VII) in the presence of about 0.8 to 1.2 mole of formic acid.

The same compound (IId) can also be produced by subjecting a compound of general formula:

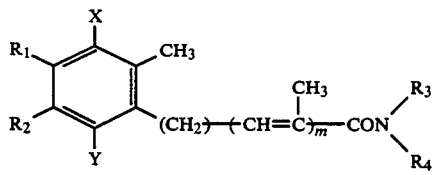
(IIe)

[wherein the symbols have the same meanings as defined hereinbefore] to reduction, for example with lithium aluminium hydride. The amount of lithium aluminium hydride used is about 2/3–2 moles per mole of compound (IIe). This reduction reaction is usually carried out in the presence of a solvent. Examples of the solvent include diethyl ether, tetrahydrofuran, etc. The reaction temperature ranges from 0° C. to the boiling point of the used solvent.

The compound of formula (I) in which Z is

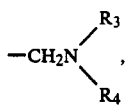

that is a compound of general formula:

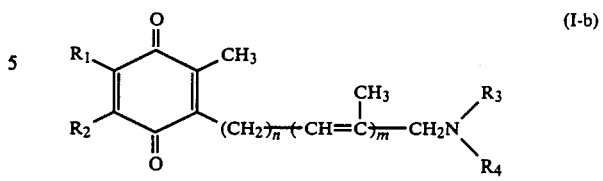
(I-b)

[wherein the symbols have the same meanings as defined above] can also be produced by subjecting a compound of formula:

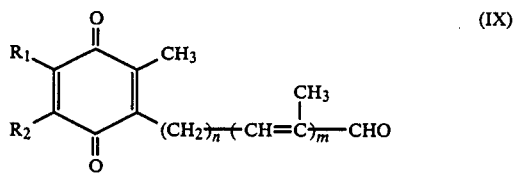
(IX)

[wherein the symbols have the same meanings as defined above] and a compound of the formula (VIII) to Leuckart-Wallach reaction. That is, a compound of the formula (IX) is reacted with a compound of the formula (VIII) in the presence of formic acid to produce a compound of the formula (I-b). This reaction is carried out in the absence or presence of a suitable solvent. Examples of the suitable solvent include alcohols such as methanol, ethanol, propanol, butanol, etc. The reaction temperature is usually 50° to 100° C., preferably 60° to 80° C. The reaction time is usually 2 to 5 hours. In this reaction, about 0.8 to 1.2 moles of compound (VIII) is contacted with one mole of compound (IX) in the presence of about 0.8 to 1.2 mole of formic acid.

The compound (I-b) thus obtained can be isolated and purified by purification and separation procedure known per se such as concentration, concentration under reduced pressure, distillation, distillation under reduced pressure, fractional distillation, pH adjustment, solvent extraction, crystallization, recrystallization, phasic transfer and chromatography.

The compound of the formula (IX) can be prepared by oxidizing a compound of the formula (VII). This reaction is carried out by a manner similar to that of the oxidation reaction of a compound of the formula (II).

EXAMPLE 1

To a solution of p-nitrophenyl 3-(2,3-dimethoxy-5-methyl-1,4-benzoquinon-6-yl)propionate (187 mg, 0.5 mmol) and glycine (37 mg, 0.5 mmol) in N,N-dimethylformamide (5 ml) was added N-ethylmorpholine (128 µl, 1.0 mmol). The mixture was stirred at room temperature for 2 days. After completion of the reaction, the solvent was distilled off under reduced pressure and the residue was chromatographed on a Sephadex, LH20 column (1.5×90 cm, eluent: ethanol). The eluate was evaporated and the residue was crystallized from ethyl ether to give 3-(2,3-dimethoxy-5-methyl-1,4-benzoquinone-6-yl)propionyl-glycine (11 mg), melting at 128°–130° C. Rf=0.34 (Chloroform-methanol-acetic acid (18:2:1), silica gel plate) (briefly Rf[1]), Rf=0.52 (Ethyl acetate-pyridine-acetic acid-water (60:20:6:10, v/v, silica gel plate) (briefly Rf[2])

Elemental analysis: Calcd. for $C_{14}H_{17}NO_7 \cdot 0.5H_2O$: C, 52.50; H, 5.66; N, 4.37. Found C, 52.75; H, 5.34; N, 4.29.

EXAMPLE 2

To a solution of p-nitrophenyl 3-(2,3-dimethoxy-5-methyl-1,4-benzoquinon-6-yl)propionate (187 mg, 0.5 mmol) and L-alanine (45 mg, 0.5 mmol) in N,N-dimethylformamide (5 ml) was added N-ethylmorpholine (128 μl, 1.0 mmol). The mixture was stirred at room temperature for 2 days. After completion of the reaction, the solvent was distilled off and the residue was chromatographed on a Sephadex LH20 column under the same conditions as above. The eluate was evaporated to give 3-(2,3-dimethoxy-5-methyl-1,4-benzoquinon-6-yl)propionyl-L-alanine (23 mg).

$[\alpha]_D^{21} -5.5°$ (c=0.5, methanol)

$Rf^1=0.48$, $Rf^2=0.66$

Elemental analysis: Calcd. for $C_{15}H_{19}NO_7$: C, 56.42; H, 6.00; N, 4.39. Found: C, 56.52; H, 6.17; N, 4.11.

EXAMPLE 3

To a solution of p-nitrophenyl 3-(2,3-dimethoxy-5-methyl-1,4-benzoquinon-6-yl)propionate (187 mg, 0.5 mmol) and L-proline (57 mg, 0.5 mmol) in N,N-dimethylformamide (5 ml) was added N-ethylmorpholine (128 μl, 1.0 mmol). The mixture was stirred at room temperature for 2 days. Thereafter, the reaction mixture was further treated in the same manner as Example 1 to give 3-(2,3-dimethoxy-5-methyl-1,4-benzoquinon-6-yl)propionyl-L-proline (81 mg), melting at 131° C.

$[\alpha]_D^{21} -38.1°$ (c=0.5, methanol)

$Rf^1=0.61$, $Rf^2=0.58$

Elemental analysis: Calcd. for $C_{17}H_{21}NO_7$: C, 58.11; H, 6.02; N, 3.99. Found: C, 57.88; H, 6.10; N, 4.24.

EXAMPLE 4

To a solution of p-nitrophenyl 3-(2,3-dimethoxy-5-methyl-1,4-benzoquinone-6-yl)propionate (187 mg, 0.5 mmol) and N-nitro-L-arginine benzyl ester di-p-toluenesulfonate (327 mg, 0.5 mmol) in N,N-dimethylformamide (5 ml) was added triethylamine (0.25 ml, 1.7 mmol). The mixture was stirred at room temperature for 15 hours. After completion of the reaction, the solvent was distilled off and the residue was chromatographed on a column of silica gel (5 g) using methanol-chloroform (1:19, v/v) as eluent. The eluate was evaporated and the residue was dissolved in acetic acid (2 ml). With palladium black catalyst (30 mg), the solution was hydrogenated at room temperature for 10 hours. After completion of the reaction, the catalyst was removed and the solvent was distilled off. Methanol (5 ml) was added to the residue and the resulting solution was ice-cooled. A solution of ferric chloride (324 mg, 2 mmol) in water (1 ml) was added and the mixture was stirred for 15 minutes. The resulting mixture was passed through a column of Amberlite XAD-2 (3 g) with water to remove the inorganic matter. Elution with methanol gave a crude compound, which was then concentrated. The residue was chromatographed on a Sephadex LR20 column (1.5×45 cm) [eluent: ethanol-0.1M acetic acid (3:2, v/v)]. The eluate was distilled off to give 3-(2,3-dimethoxy-5-methyl-1,4-benzoquinon-6-yl)propionyl-L-arginine (37 mg).

$[\alpha]_D^{21} +7.3°$ (c=0.5, methanol)

$Rf^1=0.02$, $Rf^2=0.21$

Elemental analysis: Calcd. for $C_{18}H_{26}N_4O_7 \cdot CH_3COOH$: C, 51.06; H, 6.43; N, 11.91. Found: C, 51.22; H, 6.39; N, 11.74.

EXAMPLE 5

Using p-nitrophenyl 3-(2,3-dimethoxy-5-methyl-1,4-benzoquinon-6-yl)propionate (187 mg, 0.5 mmol) and dibenzyl L-glutamate p-toluenesulfonate (250 mg, 0.5 mmol) and following the procedure of Example 4, there was obtained 3-(2,3-dimethoxy-5-methylbenzoquinon-6-yl)propionyl-L-glutamic acid (49 mg).

$[\alpha]_D^{21} -1.7°$ (c=0.5, methanol)

$Rf^1=0.22$, $Rf^2=0.49$

Elemental analysis: Calcd. for $C_{17}H_{21}NO_9$: C, 53.26; H, 5.52; N, 3.65. Found C, 53.46; H, 5.51; N, 3.50.

EXAMPLE 6

Using p-nitrophenyl 3-(2,3-dimethoxy-5-methyl-1,4-benzoquinon-6-yl)propionate (187 mg, 0.5 mmol) and O-benzyl-L-tyrosine (136 mg, 0.5 mmol) and following the procedure of Example 4, there was obtained 3-(2,3-dimethoxy-5-methyl-1,4-benzoquinon-6-yl)propionyl-L-tyrosine (43 mg), melting at 170° C.

$[\alpha]_D^{21} +20.7°$ (c=0.5, methanol)

$Rf^1=0.37$, $Rf^2=0.68$

Elemental analysis: Calcd. for $C_{21}H_{23}NO_8$: C, 60.42; H, 5.55; N, 3.36. Found: C, 60.33; H, 5.69; N, 3.47.

EXAMPLE 7

To a solution of 10-(2,3-dimethoxy-5-methyl-1,4-benzoquinon-6-yl)decanoic acid N-hydroxy-5-norbornene-2,3-dicarboxyimide ester (1.54 g, 3 mmol) and L-histidine (0.47 g, 3 mmol), in N,N-dimethylformamide (10 ml) was added triethylamine (0.42 ml, 3 mmol). The mixture was stirred at room temperature for 2 days. After completion of the reaction, the solvent was distilled off and the residue was chromatographed on a Sephadex LH 20 column (1.5×90 cm, eluent: ethanol) and the eluate was evaporated to give 10-(2,3-dimethoxy-5-methyl-1,4-benzoquinon-6-yl)decanoyl-L-histidine (136 mg).

$[\alpha]_D^{21} -5.4°$ (c=0.5, methanol), $Rf^2=0.61$

Elemental analysis: Calcd. for $C_{25}H_{35}N_3O_7$: C, 61.33; H, 7.21; N, 8.58. Found: C, 61.41; H, 7.17; N, 8.65.

EXAMPLE 8

To a solution of 10-(2,3-dimethoxy-5-methyl-1,4-benzoquinon-6-yl)decanoic acid N-hydroxy-5-norbornene-2,3-dicarboxyimide ester (1.54 g, 3 mmol) and $N^G$-nitro-L-arginine benzyl ester di-p-toluenesulfonate (1.97 g, 3 mmol) in N,N-dimethylformamide (10 ml) was added triethylamine (0.84 ml, 6 mmol). The mixture was stirred at room temperature for 15 hours. After completion of the reaction, the residue was chromatographed on a column of silica gel (20 g) [eluent: methanol-chloroform (1:19, v/v)] and the eluate was evaporated. The residue was dissolved in acetic acid (5 ml) and, the solution was hydrogenated with palladium black (100 mg) at room temperature for 10 hours. After completion of the reaction, the solvent was distilled off, the residue was dissolved in methanol (5 ml). The solution was oxidized with aqueous ferric chloride (1.95 g, 12 mmol) under ice-cooling for 15 minutes. The reaction mixture was passed through on a column of Amberlite XAD-2 (9 g) with water to remove the inorganic matter. Then elution with methanol gave a crude compound. The solvent was distilled off and the residue was chromatographed on a Sephadex LH20 column [1.5×4.5 cm; eluent: ethanol-0.1M acetic acid (3:2, v/v)]. The eluate was evaporated to give 10-(2,3-dimethoxy-5-methyl-1,4-benzoquinon-6-yl)decanoyl-L-arginine (920 mg).

$[\alpha]_D^{21}+6.4°$ (c=0.5, methanol), $Rf^1=0.03$, $Rf^2=0.27$

Elemental analysis: Calcd. for $C_{25}H_{40}N_4O_7 \cdot CH_3COOH$: C, 57.03; H, 7.80; N, 9.85. Found: C, 56.84; H, 8.05; N, 9.62.

EXAMPLE 9

Using 10-(2,3-dimethoxy-5-methyl-1,4-benzoquinone-6-yl)decanoic acid N-hydroxy-5-norbornene-2,3-dicarboxyimide ester (1.54 g, 3 mmol) and L-tryptophan benzyl ester p-toluenesulfonate (1.40 g, 3 mmol) and following the procedure of Example 8, there was obtained 10-(2,3-dimethoxy-5-methyl-1,4-benzoquinon-6-yl)decanoyl-L-tryptophan (682 mg)

$[\alpha]_D^{21}+4.9°$ (c=0.5, methanol), $Rf^1=0.87$, $Rf^2=0.85$

Elemental analysis: Calcd. for $C_{30}H_{38}H_{38}N_2O_7 \cdot \frac{1}{2}H_2O$: C, 65.80; H, 7.18; N, 5.12. Found: C, 66.00; H, 7.29; N, 5.17.

EXAMPLE 10

Using 10-(2,3-dimethoxy-5-methyl-1,4-benzoquinon-6-yl)decanoic acid N-hydroxy-5-norbornene-2,3-dicarboxyimide ester (1.54 g, 3 mmol) and $N^\epsilon$-carbobenzoxy-L-lysine benzyl ester (1.63 g, 3 mmol) and following the procedure of Example 8, there was obtained 10-(2,3-dimethoxy-5-methyl-1,4-benzoquinon-6-yl)decanoyl-L-lysine (794 mg), melting at 107° C.

$[\alpha]_D^{21}-5.8°$ (c=0.5, methanol), $Rf^1=0.03$, $Rf^2=0.19$

Elemental analysis: Calcd. for $C_{25}H_{40}N_2O_7 \cdot CH_3COOH \cdot H_2O$: C, 58.05; H, 8.30; N, 5.01. Found: C, 57.78; H, 8.29; N, 5.33.

EXAMPLE 11

Glucosamine hydrochloride (863 mg, 4 mmol) was suspended in a mixture of N,N-dimethylformamide (30 ml) and water (2 ml), followed by addition of triethylamine (0.56 ml, 4 mmol). Then, 10-(2,3-dimethoxy-5-methyl-1,4-benzoquinon-6-yl)decanoic acid N-hydroxy-5-norbornene-2,3-dicarboxyimide ester (3.08 g, 6 mmol) was added and the whole mixture was stirred at room temperature for 24 hours. After completion of the reaction, the solvent was distilled off and the residue was solidified with ethyl acetate-ethyl ether. The solid matter was collected by filtration, suspended in water (100 ml), collected by filtration and dissolved again in a small amount of methanol. Water was added and the resulting solid matter was collected by filtration to give N-[10-(2,3-dimethoxy-5-methyl-1,4-benzoquinon-6-yl)decanoyl]glucosamine (1.76 g).

Rf=0.78 (water-ethyl acetate-n-butanol-acetic acid=1:1:1:1, v/v; silica gel plate)

$[\alpha]_D^{22}+64.0°$ (c=0.5, N,N-dimethylformamide)

Elemental analysis: Calcd. for $C_{25}H_{39}NO_{10}$: C, 58.46; H, 7.66; N, 2.73. Found: C, 58.58; H, 7.58; N, 2.77.

EXAMPLE 12

To a solution of p-nitrophenyl 10-(2,3-dimethoxy-5-methyl-1,4-benzoquinon-6-yl)decanoate (4.73 g, 10 mmol) and D-phenylalanine (1.65 g, 10 mmol) in N,N-dimethylformamide (30 ml), was added triethylamine (1.4 ml, 10 mmol). The mixture was stirred at room temperature for 2 days, whereupon the insoluble matter almost disappeared. The solvent was distilled off under reduced pressure and the residue was chromatographed on a column of silica gel (100 g). The column was washed well with chloroform and elution with chloroform-methanol-acetic acid (18:2:1, v/v) gave 10-(2,3-dimethoxy-5-methyl-1,4-benzoquinon-6-yl)decanoyl-D-phenylalanine (2.56 g), melting at 96°-98° C., after washing up in the usual way.

$[\alpha]_D^{25}-8.8°$ (c=0.5, methanol), Rf=0.18 (chloroform-acetone-methanol (10:3:2, v/v, silica gel plate) (hereinafter briefly called $Rf^3$)

Elemental analysis: Calcd. for $C_{28}H_{37}NO_7$: C, 67.31; H, 7.47; N, 2.80. Found: C, 67.17; H, 7.48; N, 2.83.

EXAMPLE 13

To a solution of p-nitrophenyl 10-(2,3-dimethoxy-5-methyl-1,4-benzoquinon-6-yl)decanoate (237 mg, 0.5 mmol) and L-methionine (149 mg, 1 mmol) in N,N-dimethylformamide (1 ml) was added triethylamine (0.21 ml, 1.5 mmol). The mixture was stirred at room temperature for 16 hours. After removal of the solvent, the residue was dissolved in ethyl acetate (10 ml) and the solution was washed with 1N hydrochloric acid (5 ml×3) and saturated aqueous sodium chloride (5 ml×3) in that order and dried over anhydrous sodium sulfate. The solvent was then distilled off under reduced pressure and the residue was chromatographed on a column of silica gel (7 g). Elution was carried out with chloroform-methanol (4:1, v/v) and with chloroform-methanol-acetic acid (32:8:1, v/v) in the order mentioned. The fractions containing the desired compound were combined and the solvent was distilled off under reduced pressure to give 10-(2,3-dimethoxy-5-methyl-1,4-benzoquinon-6-yl)decanoyl-L-methionine (150 mg), melting at 83°-85° C.

$[\alpha]_D^{25}-6.6°$ (c=0.5, methanol), $Rf^1=0.79$

Elemental analysis: Calcd. for $C_{24}H_{37}NO_7S \cdot 0.5H_2O$: C, 58.51; H, 7.78; N, 2.84; S, 6.51 Found: C, 58.79; H, 7.88; N, 2.90; S, 6.41.

EXAMPLE 14

Using p-nitrophenyl 10-(2,3-dimethoxy-5-methyl-1,4-benzoquinon-6-yl)decanoate (474 mg, 1 mmol) and L-thioproline (266 mg, 2 mmol) and following the procedure of Example 13, there was obtained 10-(2,3-dimethoxy-5-methyl-1,4-benzoquinon-6-yl)decanoyl-L-thioproline (150 mg) as an oil.

$[\alpha]_D^{25}-61.2°$ (c=0.5, methanol), $Rf^1=0.74$

Elemental analysis: Calcd. for $C_{24}H_{33}O_7NS \cdot 0.5H_2O$: C, 58.99; H, 7.01; N, 2.87; S, 6.56. Found: C, 58.65; H, 7.21; N, 2.77; S, 6.54.

EXAMPLE 15

(i) t-Butyloxy-D-isoglutamine benzyl ester (3.70 g, 11 mmol) was dissolved in trifluoroacetic acid (20 ml) and the solution was stirred at room temperature for 30 minutes. The solvent was then distilled off, ether was added and the solvent was distilled off again under reduced pressure. Petroleum ether was added to the residue to give crystals, which were dried in the presence of sodium hydroxide in a desiccator, giving D-isoglutamine benzyl ester trifluoroacetate. This product was dissolved in acetonitrile (10 ml) and, under ice-cooling, the solution was neutralized with triethylamine. Then, p-nitrophenyl 10-(2,3-dimethoxy-5-methyl-1,4-benzoquinon-6-yl)decanoate (4.74 g, 10 mmol) was added and the mixture was stirred at room temperature for 16 hours. After completion of the reaction, the solvent was distilled off and the residue was dissolved in ethyl acetate (70 ml). The solution was washed with 5% aqueous solution of sodium bicarbonate (30 ml×3), 1N hydrochloric acid (30 ml×3) and saturated aqueous sodium chloride (30 ml×3) in that order and dried over anhydrous sodium sulfate. The solvent was then distilled off under reduced pressure and the residue was precipitated as a gel from ethyl acetate-ethyl ether. The same procedure was repeated twice to give 10-(2,3-dimethoxy-5-methyl-1,4-benzoquinon-6-yl)decanoyl-D-isoglutamine benzyl ester (3.74 g), melting at 83°–85° C.

$[\alpha]_D^{25} +4.4°$ (c=0.5, methanol), $Rf^3=0.68$, $Rf=0.33$ (chloroform-methanol=19:1, v/v, silica gel plate) (briefly $Rf^4$)

Elemental analysis: Calcd. for $C_{31}H_{42}N_2O_8$: C, 65.24; H, 7.42; N, 4.91. Found: C, 65.29; H, 7.36; N, 4.97.

(ii) 10-(2,3-Dimethoxy-5-methyl-1,4-benzoquinon-6-yl)decanoyl-D-isoglutamine benzyl ester (3.42 g, 6 mmol) was dissolved in methanol (12 ml) and, the solution was hydrogenated with palladium black at room temperature for 3 hours. After completion of the reaction, the solvent was distilled off and the residue was dissolved in methanol (25 ml). A solution of ferric chloride (2.43 g, 15 mmol) in water (5 ml) was added and the mixture was stirred at room temperature for 10 minutes. The solvent was then distilled off and the residue was dissolved in ethyl acetate (30 ml), washed with water (15 ml×4) and dried over anhydrous sodium sulfate. The solvent was distilled off under reduced pressure and the residue was chromatographed on a silica gel column. Elution with chloroform-methanol (9:1, v/v), chloroform-acetone-methanol (10:3:2, v/v) and chloroform-methanol-acetic acid (18:2:1, v/v) in that order gave a crude product. The product was recrystallized from ethanol-ethyl ether-petroleum ether to give 10-(2,3-dimethoxy-5-methyl-1,4-benzoquinon-6-yl)decanoyl-D-isoglutamine (1.61 g), melting at 136°–137° C.

$[\alpha]_D +7.0°$ (c=0.5, methanol)
$Rf^1=0.47$, $Rf^4=0.09$

Elemental analysis: Calcd. for $C_{24}H_{36}N_2O_8$: C, 59.98; H, 7.55; N, 5.83. Found: C, 59.74; H, 7.57; N, 5.95.

EXAMPLE 16

To a solution of 10-(2,3-dimethoxy-5-methyl-1,4-benzoquinon-6-yl)decanoic acid (176 mg, 0.5 mmol), diphenylmethyl N-acetyl-1-O-benzyl-α-muraminate (275 mg, 0.5 ml) and toluenesulfonic acid (10 mg) in anhydrous pyridine (1 ml) was added N,N-dicyclohexylcarbodiimide (206 mg, 1 mmol). The reaction was conducted at room temperature for 90 minutes. The precipitate was filtered off and the solvent was distilled off. The residue was purified by preparative silica gel thin layer chromatography using chloroform-methanol (49:1, v/v) as solvent to give diphenylmethyl N-acetyl-1-O-benzyl-6-O-[10-(2,3-dimethoxy-5-methyl-1,4-benzoquinon-6-yl)decanoyl]-α-muraminate (142 mg) as an oil. $Rf^4=0.88$. This oil (142 mg) was hydrogenated in the presence of palladium black in acetic acid (5 ml) at room temperature for 8 hours. The catalyst was filtered off and the solvent was distilled off. The residue was dissolved in dioxane (5 ml), a solution of ferric chloride (400 mg) in water (0.5 ml) was added, and the mixture was stirred at room temperature for 30 minutes. The reaction mixture was extracted with water (20 ml) and ethyl acetate (20 ml) and the organic layer was washed with water and dried over anhydrous sodium sulfate. The solvent was distilled off and the residue was purified by preparative silica gel thin layer chromatography (eluent: the solvent system for $Rf^1$). After elution, the portion containing the desired compound was scraped off and the extracted with methanol. The methanol was distilled off and the residue was dissolved in ethyl acetate, washed with water and dried over anhydrous sodium sulfate. The solvent was then distilled off to give N-acetyl-6-O-[10-(2,3-dimethoxy-5-methyl-1,4-benzoquinon-6-yl)decanoyl]muraminic acid (104 mg).

$[\alpha]_D^{21} +34.4°$ (c=0.5, ethanol), $Rf^1=0.26$

Elemental analysis: Calcd. for $C_{30}H_{45}NO_{13}.0.5H_2O$: C, 56.59; H, 7.28; N, 2.20. Found: C, 56.52; H, 7.40; N, 2.25.

EXAMPLE 17

Compound 10 (1.72 g, 4 mmol) as obtained in Reference Example 1 and 2,6-dicarboxypyridine N-oxide (2.20 g, 21 mmol) were dissolved in 30% aqueous acetonitrile (50 ml) and the solution was stirred under ice-cooling. To the mixture was added dropwise an ice-cooled solution of ammonium cerium (IV) nitrate (6.58 g, 12 mmol) in 50% aqueous acetonitrile (30 ml) over 30 minutes and the mixture was stirred under the same conditinos for 30 minutes and then at room temperature for 30 minutes. After completion of the reaction, the insoluble matter was filtered off and washed well with ethyl acetate (100 ml). The filtrate and washings were combined and the solvent was distilled off under reduced pressure. The residue was treated with ethyl acetate (150 ml) and water (50 ml) to extract the product therefrom. The organic layer was washed with aqueous sodium chloride and dried ($MgSO_4$), and the organic solvent was distilled off under reduced pressure. The residue was chromatographed on a silica gel column and elution with ethyl acetate-isopropyl ether (1:1) gave 4-{4-[6-(2,3-dimethoxy-5-methyl-1,4-benzoquinonyl)]butoxy}cinnamic acid (Compound 1, 1.05 g).

Using the compounds 12, 14, 16, 18, 19, 20 and 21 as obtained in Reference Examples 1, 6 and 7 and following the same procedure as above, there were obtained the following compounds 2–8.

Compound 2

4-[4-{6-(2,3-dimethoxy-5-methyl-1,4-benzoquinonyl)}-2-methyl-2-butenoxy]cinnamic acid

Compound 3

4-[6-(2,3-dimethoxy-5-methyl-1,4-benzoquinonyl)]methoxycinnamic acid

Compound 4

4-[4-{6-(2,3-dimethoxy-5-methyl)-1,4-benzoquinonyl)}-2-methyl-2-butenxoy]phenylacetic acid

Compound 5

4-[4-(6-2,3-dimethoxy-5-methyl-1,4-benzoquinonyl)-]methoxyphenylacetic acid

Compound 6

2-[4-{6-(2,3-dimethoxy-5-methyl-1,4-benzoquinonyl)}methoxyphenyl]propionic acid

Compound 7

3-[6-(2,3-dimethoxy-5-methyl-1,4-benzoquinonyl)]acrylic acid

Compound 8

1-[6-(2,3-dimethoxy-5-methoxy-1,4- benzoquinonyl)]-3-oxo-1-butene

Table 3 shows the physical properties and constants of the Compounds 1–8 described above.

TABLE 3

| Compound | Molecular formula (molecular weight) Elemental analysis | Melting point (°C.) | EM-390NMR (TMS as internal standard) δ value |
|---|---|---|---|
| 1 | $C_{22}H_{24}O_7$ (400.43)<br>Calcd. C, 65.99; H, 6.04<br>Found C, 65.92; H, 5.84 | 153~155° C. | ($d_6$-DMSO) 1.4~2.0 (4H), 1.95 (3H), 2.46 (2H), 3.88 (6H), 4.01 (2H), 6.30 (1H), 6.93 (2H), 7.53 (1H), 7.58 (2H). |
| 2 | $C_{23}H_{24}O_7$ (412.45)<br>Calcd. C, 66.98; H, 5.87<br>Found C, 66.93; H, 5.86 | 141~144° C. | ($CDCl_3$) 1.86 (3H), 2.01 (3H), 3.27 (2H), 3.98 (6H), 4.40 (2H), 5.39 (1H), 6.29 (1H), 6.88 (2H), 7.48 (2H), 7.74 (1H). |
| 3 | $C_{19}H_{18}O_7$ (358.35)<br>Calcd. C, 63.68; H, 5.06<br>Found C, 63.30; H, 5.27 | 190~192° C. | ($d_6$-DMSO) 2.05 (3H), 3.93 (6H), 4.93 (2H), 6.34 (1H), 7.02 (2H), 7.56 (1H), 7.63 (2H). |
| 4 | $C_{22}H_{24}O_7$ (400.43)<br>Calcd. C, 65.99; H, 6.04<br>Found C, 66.08; H, 6.15 | 92~94° C. | ($CDCl_3$) 1.84 (3H), 2.00 (3H), 3.26 (2H), 3.54 (2H), 3.98 (6H), 4.34 (2H), 5.36 (1H), 6.82 (2H), 7.16 (2H), 7.71 (1H). |
| 5 | $C_{18}H_{18}O_7$ (346.34)<br>Calcd. C, 62.42; H, 5.24<br>Found C, 62.10; H, 5.08 | 107~110° C. | ($CDCl_3$) 2.13 (3H), 3.57 (2H), 3.99 (3H), 4.01 (3H), 4.92 (2H), 6.89 (2H), 7.22 (2H). |
| 6 | $C_{19}H_{20}O_7$ (360.37)<br>Calcd. C, 63.33; H, 5.59<br>Found C, 63.43; H, 5.68 | Oily substance | ($CDCl_3$) 1.47 (3H), 2.14 (3H), 3.67 (1H), 4.02 (6H), 4.93 (2H), 6.8~7.4 (4H). |
| 7 | $C_{12}H_{12}O_6$ (252.23)<br>Calcd. C, 57.14; H, 4.80<br>Found C, 56.85; H, 4.84 | 113~116° C. | ($CDCl_3$) 2.20 (3H), 4.02 (6H), 6.78 (1H), 7.66 (1H). |
| 8 | $C_{13}H_{14}O_5$ (250.26)<br>Calcd. C, 62.39; H, 5.64<br>Found C, 62.19; H, 5.77 | 85~86° C. | ($CDCl_3$) 2.17 (3H), 2.35 (3H), 4.01 (6H), 6.93 (1H), 7.40 (1H). |

EXAMPLE 18

2,3-Dimethoxy-5-methyl-1,4-bismethoxymethyloxy-6-(8-methoxycarbonyl-1,3,5,7-octatetraenyl)benzene (0.43 g, 1 mmol) as obtained in Reference Example 4 was dissolved in acetone (5 ml), and 2N sulfuric acid (1 ml) was added. The reaction was conducted under reflux at 70° C. for an hour. The acetone was distilled off under reduced pressure and the residue was extracted with ethyl acetate (25 ml) and water (10 ml). The ethyl acetate layer was concentrated under reduced pressure and the residue was dissolved in tetrahydrofuran (5 ml). A 1M aqueous ferric chloride solution (2.0 ml) was added and the mixture was stirred at room temperature for 30 minutes. After completion of the reaction, the tetrahydrofuran was distilled off under reduced pressure, and the residue was extracted with ethyl acetate (50 ml) and water (30 ml) to extract the product therefrom. The organic layer was washed with aqueous sodium chloride, dried ($MgSO_4$) and concentrated. The residue was recrystallized from ethyl acetate-isopropyl ether (1:1) to give methyl 9-[6-(2,3-dimethoxy-5-methyl-1,4-benzoquinonyl)]-2,4,6,8-nonatetraenoate (0.21 g).

mp. 155°–156° C. δ 2.13(3H), 3.74(3H), 3.99(3H), 4.01(3H), 5.92(1H), 6.4–6.7(5H), 7.2–7.5(2H).

Elemental analysis: Calcd. for $C_{19}H_{20}O_6$ (344.37): C, 66.27; H, 5.85. Found: C, 65.98; H, 5.85.

EXAMPLE 19

2-Benzoxazolepropionic acid (0.90 g, 2.44 mmol) obtained in Reference Example 5 and silver oxide (AgO, 1.21 g, 9.76 mmol) were suspended in dioxane (25 ml) and the suspension was cooled to 10° C. 6N nitric acid (2.44 ml) was added dropwise over 10 minutes. The mixture was stirred under the same conditions for 30 minutes and the dioxane was distilled off under reduced pressure. To the residue were added ethyl acetate (50 ml) and water (30 ml) and the mixture was filtered with the aid of Celite to remove the insoluble matter. The ethyl acetate layer was washed with water and dried ($MgSO_4$), and the solvent was distilled off under reduced pressure. The residue was chromatographed on silica gel column using ethyl acetate to give 2-[2-{6-(2,3,5-trimethyl-1,4-benzoquinonyl)}benzoxazol-6-yl]propionic acid (0.40 g)

δ 1.58(3H), 2.10(6H), 2.21(3H), 3.89(1H), 7.39(1H), 7.57(1H), 7.82(1H)

Elemental analysis: Calcd. for $C_{19}H_{17}NO_5$ (339.35): C, 67.25; H, 5.05; N, 4.13. Found: C, 67.14; H, 5.22; N, 4.01.

EXAMPLE 20

Silver oxide (15 g) was added to a solution of 2,3-dimethoxy-5-methyl-6-morpholinomethylhydroquinone (9 g) as obtained in Reference Example 8 in ether-dioxane (5:2, 70 ml) and the mixture was stirred at room temperature for 1.5 hours. The filtrate was treated in the conventional manner and the residue was recrystallized from ethyl acetate-hexane to give 2,3-dimethoxy-5-methyl-6-morpholinomethyl-1,4-benzoquinone (4.5 g), melting at 60°–62° C.

Elemental analysis: Calcd. for $C_{14}H_{19}O_5N$: C, 59.77; H, 6.81; N, 4.98. Found: C, 59.87; H, 6.75; N, 4.80.

A solution of 1% hydrochloric acid in methanol (15 ml) was added to the above product (1.2 g). After evaporation to dryness, the residue was recrystallized from methanol-ether to give the hydrochloride (1.19 g), melting at 155°–164° C.

Elemental aalysis: Calcd. for $C_{14}H_{19}O_5N.HCl$ C, 52.91; H, 6.34; N, 4.41. Found: C, 52.80; H, 6.48; N, 4.35.

EXAMPLE 21

6-(9-Formylnonyl)-2,3-dimethoxy-5-methyl-1,4-benzoquinone (0.9 g) as obtained in Reference Example 9 was added portionwise to a solution of morpholine formate (0.43 g) in methanol (5 ml) and the mixture was warmed at 60°–80° C. for one hour. An additional amount of morpholine formate (0.2 g) was added and the mixture was warmed at the same temperature for an hour. The reaction mixture was poured into an ice water and extraction was carried out with ethyl acetate. The extract was treated in the conventinoal manner and the residue was purified by silica gel column chromatography, elution being carried out with hexane-ethyl acetate (4:1). The eluate was evaporated to dryness and an equimolar amount of hydrochloric acid in methanol was added to the residue. The methanol was evaporated and the residue was recrystallized from methanol-ether to give 6-morpholinodecyl-2,3-dimethoxy-5-methyl-1,4-benzoquinone hydrochloride, melting at 101°–103° C.

Elemental analysis: Calcd. for $C_{23}H_{37}O_5N.HCl$: C, 62.22; H, 8.13; N, 3.16. Found: C, 61.98; H, 8.33; N, 3.03.

EXAMPLE 22

6-(9-Formylnonyl)-2,3-dimethoxy-5-methyl-1,4-benzoquinone (0.4 g) as obtained in Reference Example 9 was added portionwise to a solution of dimethylamine formate (0.12 g) in methanol (1 ml) and the mixture was warmed at 60°–80° C. for 3.5 hours. An additional amount of dimethylamine formate (0.05 g) was added and thereafter the mixture was further treated in the same manner as in Example 21. The residue was dissolved in ethyl acetate and a solution of oxalic acid in ethyl acetate was added. The crystalline precipitate was collected by filtration and recrystallized from methanol-ether to give 6-dimethylaminodecyl-2,3-dimethoxy-5-methyl-1,4-benzoquinone oxalate.

Elemental analysis: Calcd. for $C_{21}H_{35}O_4N.C_2H_2O_4$ C, 60.63; H, 8.19; N, 3.08. Found: C, 60.43; H, 8.03; N, 3.34.

EXAMPLE 23

Using 6-(4-dimethylaminobutyl)-2,3-dimethoxy-5-methyl-hydroquinone as obtained in Reference Example 10 and following the procedure of Example 20, there was obtained 6-dimethylaminobutyl-2,3-dimethoxy-5-methyl-1,4-benzoquinone.

The product was dissolved in methanol and to the solution was added a solution of oxalic acid (molar equivalent) in methanol. The mixture was concentrated and the product was crystallized from methanol-ether to give oxalic acid ester of 6-dimethylaminobutyl-2,3-dimethoxy-5-methyl-1,4-benzoquinone.

δ 1.33–1.90(4H), 2.00(3H), 2.50(2H), 2.85(6H), 3.00–3.20 (2H), 3.95(6H)

EXAMPLE 24

By the same manner as Example 20, 2,3-dimethoxy-5-methyl-6-dimethylaminomethylhydroquinone (2 g) obtained in Reference Example 11 was oxidized with silver oxide. Quinone compound obtained in the usual way was dissolved in ether (20 ml) and to this solution was added methanol solution of hydrochloric acid. The mixture was concentrated to dryness. The residue was recrystallized from methanol-ether to give 2,3-dimethoxy-5-methyl-6-dimethylaminomethyl-1,4-benzoquinone hydrochloride (1.45 g) m.p. 139°–145° C.

Elemental analysis: Calcd. for $C_{12}H_{17}O_4N.HCl$ C, 52.27; H, 6.58; N, 5.08. Found: C, 52.06; H, 6.58; N, 4.93.

REFERENCE EXAMPLE 1

(a) A solution of 1,2,3,4-tetramethoxy-5-methyl-6-(4-iodobutyl)benzene (3.94 g, 10 mmol) in dimethylformamide (10 ml) was added to a suspension of ethyl p-hydroxycinnamate (1.92 g, 10 mmol) and 60% sodium hydride in oil (0.42 g, 10.5 mol) in dimethylformamide (18 ml) at room temperature. The mixture was stirred for 30 minutes. After completion of the reaction, the reaction mixture was extracted by addition of 2% aqueous phosphoric acid (50 ml) and isopropyl ether (50 ml). The extract was concentrated and the residue was chromatographed on a silica gel column eluting with isopropyl ether to give ethyl 4-[4-(2,3,4,5-tetramethoxy-6-methylphenyl)buthoxy]cinnamate (Compound 9, 4.51 g). This ethyl ester (2.00 g, 4.37 mmol) was dissolved in an aqueous tetrahydrofuran-methanol solution (25 ml) and hydrolized with sodium hydroxide (0.35 g, 8.75 mmol). The solution was allowed to stand at 50° C. overnight. The reaction mixture was acidified with dilute phosphoric acid and the product was extracted with ethyl acetate. The organic layer was dried (MgSO4) and concentrated under reduced pressure. The residue was recrystallized from ethyl acetate-isopropyl ether to give 4-[4-(2,3,4,5-tetramethoxy-6-methylphenyl)buthoxy]cinnamic acid (Compound 10, 1.78 g).

(b) Using 1,2,3,4-tetramethoxy-5-methyl-6-(4-chloro-3-methyl-2-butenyl)benzene and methyl p-hydroxycinnamate and following the procedure described above, there were obtained methyl 4-[4-(2,3,4,5-tetramethoxy-6-methylphenyl)-2-methyl-2-butenyloxy]cinnamate (Compound 11) and 4-[4-(2,3,4,5-tetramethoxy-6-methylphenyl)-2-methyl-2-butenyloxy]cinnamic acid (Compound 12).

(c) Using 1,2,3,4-tetramethoxy-5-methyl-6-bromomethylbenzene and methyl p-hydroxycinnamate and following the procedure described above, there were obtained methyl 4-(2,3,4,5-tetramethoxy-6-methylbenzyloxy)cinnamate (Compound 13) and 4-(2,3,4,5-tetramethoxy-6-methylbenzyloxy)cinnamic acid (Compound 14).

(d) Using 1,2,3,4-tetramethoxy-5-methyl-6-(4-chloro-3-methyl-2-butenyl)benzene and methyl p-hydroxyphenylacetate and following the procedure described above, there were obtained methyl 4-[4-(2,3,4,5-tetramethoxy-6-methylphenyl)-2-methyl-2-butenyloxy]phenylacetate (Compound 15) and 4-[4-(2,3,4,5-tetramethoxy-6-methylpheny)-2-methyl-2-butenyloxy]phenylacetic acid (Compound 16).

(e) Using 1,2,3,4-tetramethoxy-5-methyl-6-bromobenzene and methyl p-hydroxyphenylacetate and following the procedure described above, there were obtained methyl 4-(2,3,4,5-tetramethoxy-6-methylbenzyloxy)phenylacetate (Compound 17) and 4-(2,3,4,5-tetramethoxy-6-methylbenzyloxy)phenylacetic acid (Compound 18).

Table 4 shows their physical and spectral properties of the above Compounds 9–18.

TABLE 4

| Compound | Molecular formula (molecular weight) Elemental analysis | Melting point (°C.) | EM-390NMR (TMS as internal standard) δ value |
|---|---|---|---|
| 9 | $C_{26}H_{34}O_7$ (458.56)<br>Calcd. C, 68.10; H, 7.47<br>Found C, 68.05; H, 7.53 | Oily substance | (CDCl₃) 1.32 (3H), 1.5~2.0 (4H), 2.17 (3H), 2.66 (2H), 3.77 (3H), 3.81 (3H), 3.89 (6H), 4.03 (2H), 4.25 (2H), 6.29 (1H), 6.89 (2H), 7.48 (2H), 7.66 (1H). |
| 10 | $C_{24}H_{30}O_7$ (430.50) | 152~4° C. | (d₆-DMSO) 1.4~2.0 (4H), 2.11 (3H), |

TABLE 4-continued

| Compound | Molecular formula (molecular weight) Elemental analysis | Melting point (°C.) | EM-390NMR (TMS as internal standard) δ value |
|---|---|---|---|
|  | Calcd. C, 66.96; H, 7.02<br>Found C, 66.99; H, 7.08 |  | 2.59 (2H), 3.69 (3H), 3.73 (3H), 3.80 (6H), 4.04 (2H), 6.30 (1H), 6.94 (2H), 7.54 (1H), 7.57 (2H). |
| 11 | $C_{26}H_{32}O_7$ (456.54)<br>Calcd. C, 68.40; H, 7.06<br>Found C, 68.57; H, 7.18 | Oily substance | (CDCl$_3$) 1.87 (3H), 2.11 (3H), 3.39 (2H), 3.77 (9H), 3.88 (6H), 4.40 (2H), 5.47 (1H), 6.27 (1H), 6.88 (2H), 7.43 (2H), 7.64 (1H). |
| 12 | $C_{25}H_{30}O_7$ (442.52)<br>Calcd. C, 67.86; H, 6.83<br>Found C, 68.01; H, 6.84 | 117~8° C. | (CDCl$_3$) 1.89 (3H), 2.13 (3H), 3.40 (2H), 3.78 (6H), 3.90 (6H), 4.43 (2H), 5.49 (1H), 6.30 (1H), 6.90 (2H), 7.47 (2H), 7.75 (1H). |
| 13 | $C_{22}H_{26}O_7$ (402.45)<br>Calcd. C, 65.66; H, 6.51<br>Found C, 65.65; H, 6.42 | 98~99° C. | (CDCl$_3$) 2.23 (3H), 3.78 (3H), 3.80 (3H), 3.83 (3H), 3.90 (3H), 3.93 (3H), 5.07 (2H), 6.31 (1H), 7.03 (2H), 7.51 (2H), 7.69 (1H). |
| 14 | $C_{21}H_{24}O_7$ (388.42)<br>Calcd. C, 64.94; H, 6.23<br>Found C, 64.89; H, 6.31 | 179~181° C. | (CDCl$_3$) 2.26 (3H), 3.81 (3H), 3.83 (3H), 3.91 (3H), 3.94 (3H), 5.08 (2H), 6.33 (1H), 7.05 (2H), 7.55 (2H), 7.79 (1H). |
| 15 | $C_{25}H_{32}O_7$ (444.53)<br>Calcd. C, 67.55; H, 7.26<br>Found C, 67.32; H, 7.18 | Oily substance | (CDCl$_3$) 1.87 (3H), 2.12 (3H), 3.39 (2H), 3.52 (2H), 3.66 (3H), 3.77 (6H), 3.89 (6H), 4.38 (2H), 5.47 (1H), 6.83 (2H), 7.16 (2H). |
| 16 | $C_{24}H_{30}O_7$ (430.50)<br>Calcd. C, 66.96; H, 7.02<br>Found C, 66.83; H, 7.21 | Oily substance | (CDCl$_3$) 1.87 (3H), 2.10 (3H), 3.38 (2H), 3.53 (2H), 3.77 (6H), 3.89 (6H), 4.37 (2H), 5.45 (1H), 6.83 (2H), 7.16 (2H). |
| 17 | $C_{21}H_{26}O_7$ (390.44)<br>Calcd. C, 64.60; H, 6.71<br>Found C, 64.38; H, 6.65 | Oily substance | (CDCl$_3$) 2.23 (3H), 3.56 (2H), 3.68 (3H), 3.80 (3H), 3.82 (3H), 3.90 (3H), 3.93 (3H), 5.00 (2H), 6.98 (2H), 7.23 (2H). |
| 18 | $C_{20}H_{24}O_7$ (376.41)<br>Calcd. C, 63.82; H, 6.43<br>Found C, 63.84; H, 6.57 | Oily substance | (CDCl$_3$) 2.24 (3H), 3.59 (2H), 3.81 (3H), 3.83 (3H), 3.91 (3H), 3.94 (3H), 5.02 (2H), 7.00 (2H), 7.25 (2H). |

REFERENCE EXAMPLE 2

4-(2,3,4,5-Tetramethoxy-6-methylbenzyloxy)-phenylacetic acid (2.07 g, 5.5 mmol) was dissolved in tetrahydrofuran-hexamethylphosphoramide (10:1, 11 ml). A solution of lithium diisopropylamide in tetrahydrofuran-hexane (20 ml, 2 equivalents) was cooled to −20° C. and the above-mentioned solution was added to this solution. The mixture was stirred for 30 minutes and then, after addition of methyl iodide (0.85 g, 60 mmol), it was stirred for 1.5 hours, while the reaction temperature was gradually raised from −20° C. to 0° C. After completion of the reaction, extraction and isolation conducted in a conventional manner gave 2-[4-(2,3,4,5-tetramethoxy-5-methylbenzyloxy)phenyl]propionic acid (Compound 19).

[Oily substance, δ 1.49(3H), 2.23(3H), 3.69(1H), 3.80(3H), 3.82(3H), 3.89(3H), 3.92(3H), 5.00(2H), 6.99(2H), 7.28(2H)]

REFERENCE EXAMPLE 3

To a cold solution of 2,3-dimethoxy-5-methyl-1,4-bismethoxymethyloxy-6-bromobenzene [oily substance, δ 2.34 (3H), 3.57 (3H), 3.64 (3H), 3.84 (6H), 5.01 (2H), 5.09 (2H)] (9.00 g, 25.6 mmol) in absolute ether (90 ml) was added a solution of 15% n-butyllithium in hexane (17.6 ml). The mixture was stirred for 30 minutes. Dimethylformamide (9.36 g, 128 mmol) was added and the reaction was continued under the same conditions for 30 minutes. Working up in a conventional manner gave 2,3-dimethoxy-5-methyl-1,4-bismethoxymethyloxy-6-formylbenzene [oily substance, δ2.48 (3H), 3.55 (3H), 3.58 (3H), 3.85 (3H), 3.95 (3H), 4.99 (2H), 5.13 (2H)]. Yield 80%.

REFERENCE EXAMPLE 4

Trimethylphosphonocrotonate (3.82 g, 18.4 mmol) was dissolved in tetrahydrofuran (20 ml). Lithiumdiisopropylamide (tetrahydrofuran-hexane, 1.15 equivalents) was cooled to −20° C. and the above-mentioned solution was added thereto. To this phosphonoylide solution was added a solution of the formyl compound (6.00 g, 16.7 mmol) as obtained in Reference Example 3 in tetrahydrofuran (30 ml), and the reaction was conducted under the same conditions for 15 minutes and then continued at −20° C. to 0° C. for 30 minutes. Working up in usual manner gave 2,3-dimethoxy-5-methyl-1,4-bismethoxymethyloxy-6-(4-methoxycarbonyl-1,3-butadienyl)benzene [oily substance, δ 2.27 (3H), 3.49 (3H), 3.58 (3H), 3.76 (3H), 3.86 (3H), 3.88 (3H), 5.04 (4H), 5.95 (1H), 6.90 (1H), 6.96 (1H), 7.3–7.6 (1H)]. Yield, 90%. This methyl ester (5.74 g, 15.0 mmol) was reduced with diisobutylaluminum hydride (hexane solution, 34.1 ml, 60 mmol) in absolute ether at −70° C. Working up in the usual manner gave 2,3-dimethoxy-5-methyl-1,4-bismethoxymethyloxy-6-(5-hydroxy-1,3-pentadienyl)benzene [oily substance, δ 1.62 (1H), 2.24 (3H), 3.50 (3H), 3.57 (3H), 3.87 (6H), 4.24 (2H), 5.00 (2H), 5.04 (2H), 5.8–6.1 (1H), 6.35 (1H), 6.5–6.7 (1H)]. Yield 97%.

The alcohol compound (4.85 g, 13.7 mmol) prepared as above was dissolved in methylene chloride and the mixture was oxidized with active manganese dioxide (14.6 g) at room temperature for 2 hours. Working up in usual way gave 2,3-dimethoxy-5-methyl-1,4-bismethoxymethyloxy-6-(4-formyl-1,3-butadienyl)benzene [oily substance δ 2.30 (3H), 3.49 (3H), 3.58 (3H), 3.86 (3H), 3.89 (3H), 5.06 (4H), 6.23 (1H), 7.0–7.4 (3H), 9.65 (1H)]. Yield 93%.

The dienealdehyde compound (4.50 g, 12.8 mmol) obtained as above was reacted with trimethylphosphonocrotonatoylide under the same conditions as described above. Working up in usual way gave 2,3-dimethoxy-5-methyl-1,4-bismethoxymethyloxy-6-(8-methoxy-carbonyl-1,3,5,7-octatetraenyl)benzene [mp. 51°–52° C., δ 2.27 (3H), 3.50 (3H), 3.58 (3H), 3.73 (3H), 3.88 (6H), 5.03 (2H), 5.05 (2H), 5.88 (1H), 6.2–6.9 (6H), 7.2–7.4 (1H)]. Yield 48%.

REFERENCE EXAMPLE 5

2,5-Dimethoxy-3,4,6-trimethylbenzoic acid (m.p. 98°–100° C.) was reacted with methyl 3-amino-4-hydroxyphenylacetate to give methyl 4-hydroxy-3-(2,5-dimethoxy-3,4,6-trimethylbenzoylamino)phenylacetate [m.p. 159°–160° C., δ 2.14 (3H), 2.20 (3H), 2.32 (3H), 3.48 (2H), 3.65 (6H), 3.70 (3H), 7.02 (3H), 8.30 (1H), 8.87 (1H)] (11.0 g, 28.4 mmol), which was dehydrated with phosphorus oxychloride (13.1 g) to give methyl 2-[6-(2,5-dimethoxy-3,4,6-trimethylphenyl)benzoxazol-6-yl]acetate m.p. 68°–69° C., δ 2.22 (3H), 2.27 (3H), 3.58 (3H), 3.70 (3H), 3.72 (3H), 3.76 (2H), 7.32 (1H), 7.55 (1H), 7.76 (1H)].

To a solution of tetrabutylammonium hydrogen sulfate (3.40 g, 10 mmol) and sodium hydroxide (0.80 g, 20 mmol) in water (10 ml) were added a solution of the benzoxazole compound (1.85 g, 5.0 mmol) obtained as above in dichloromethane (10 ml) and methyl iodide (5.68 g, 40 mmol). The mixture was stirred vigorously at room temperature for 4 hours. After the reaction, the dichloromethane layer was separated and the dichloromethane was distilled off under reduced pressure. To the residue was added isopropyl ether (100 ml) and the insoluble matter was filtered off. The isopropyl ether was then distilled off under reduced pressure and the residue was chromatographed on a silica gel column, elution being carried out with isopropyl ether-hexane to give the corresponding methyl benzoxazolepropionate [oily substance 0.86 g, δ 1.57 (3H), 2.20 (6H), 2.27 (3H), 3.58 (3H), 3.69 (6H), 3.86 (1H), 7.32 (1H), 7.54 (1H), 7.76 (1H)].

This methyl ester compound was hydrolyzed with sodium hydroxide in a conventional manner to give the corresponding benzoxazolepropionic acid [δ 1.59 (3H), 2.19 (3H), 2.21 (3H), 2.27 (3H), 3.57 (3H), 3.68 (3H), 3.89 (1H), 7.34 (1H), 7.55 (1H), 7.82 (1H), 10.09 (1H)].

REFERENCE EXAMPLE 6

2,3,4,5-Tetramethoxy-6-methylbenzaldehyde (17.3 g, 72.1 mmol), malonic acid (22.5 g, 216 mmol) and piperidine (1.7 ml) were dissolved in pyridine (50 ml). The reaction was conducted for 5 hours, while the temperature was gradually raised from 50° C. to 100° C. The solvent was removed under reduced pressure. The residue was acidified with 2N hydrochloric acid, extracted and concentrated. Recrystallization of the product from ethyl acetate-isopropyl ether gave 1,2,3,4-tetramethoxy-5-methylcinnamic acid (Compound 20, 14.3 g, 70%). m.p. 117°–118° C. δ 2.31 (3H), 3.78 (3H), 3.83 (3H), 3.90 (3H), 3.96 (3H), 6.59 (1H), 7.94 (1H), 11.2 (1H).

REFERENCE EXAMPLE 7

To a solution of 2,3,4,5-tetramethoxy-6-methylbenzaldehyde (1.56 g, 6.5 mmol) and acetone (1.13 g, 19.5 mmol) in methanol (15 ml) was added 28% methanolic sodium methoxide (1.88 g). The mixture was refluxed for 1.5 hours. After completion of the reaction, the mixture was concentrated under reduced pressure. The residue was chromatographed on a silica gel column, elution being carried out with isopropyl ether. The fractions containing the desired compound were concentrated to give 1,2,3,4-tetramethoxy-5-methyl-6-(3-oxo-1-butenyl)benzene (Compound 21, 1.09 g, 60% Oily substance) δ 2.28 (3H), 2.36 (3H), 3.77 (3H), 3.79 (3H), 3.89 (3H), 3.95 (3H), 6.70 (1H), 7.57 (1H),

REFERENCE EXAMPLE 8

A solution of 2,3-dimethoxy-5-methyl-1,4-benzohydroquinone (2.2 g), 37% formaldehyde (2.4 ml) and morpholine (2.4 ml) in dioxane (11 ml) was refluxed at 100° C. for 2 hours. The reaction mixture was evaporated to dryness and the residue was suspended in water. The suspension was extracted with chloroform and the extract was treated in a conventional manner. The residue was recrystallized from ether-hexane to give 2,3-dimethoxy-5-methyl-6-morpholinomethylhydroquinone (2.23 g), melting at 127°–130° C.

Elemental analysis: Calcd. for $C_{14}H_{21}O_5N$: C, 59.35, H, 7.47; N, 4.94. Found: C, 59.66; H, 7.44; N, 5.00.

REFERENCE EXAMPLE 9

Pyridinium chlorochromate (3.3 g) and sodium acetate (0.5 g) were suspended in dichloromethane (2.5 ml). To the suspension was added a solution of 6-(10-hydroxydecyl)-2,3-dimethoxy-5-methyl-1,4-benzoquinone (3.38 g) in dichloromethane (20 ml) at room temperature. The mixture was stirred for an hour. Then, additional amount of pyridinium chlorochromate (1 g) and sodium acetate (0.5 g) were added and the mixture was stirred for another 1.5 hours. The reaction mixture was poured into an ice water and the mixture was extracted with ethyl acetate. The extract was treated in a conventional manner and the residue obtained was purified by column chromatography using silica gel. Elution was carried out with dichloroethane-ethyl acetate (9:1) and then with carbon tetrachloride-ethyl acetate (9:1), and the eluate was recrystallized from ethyl acetate-hexane to give 6-(9-formylnonyl)-2,3-dimethoxy-5-methyl-1,4-benzoquinone (1.3 g), melting at 44.5°–46.5° C.

Elemental analysis: Calcd. for $C_{19}H_{28}O_5$: C, 67.83; H, 8.39. Found: C, 67.73; H, 8.27.

REFERENCE EXAMPLE 10

A suspension of 6-(3-carboxypropyl)-2,3-dimethoxy-5-methyl-1,4-benzoquinone (1 g), zinc powder (1.22 g), pyridine (1 ml) and acetic anhydride (1 ml) was stirred for 12 hours. The insolubles were filtered off and the filtrate was evaporated to dryness under reduced pressure. The residue was suspended in water (20 ml) and the suspension was stirred at room temperature for 12 hours. The reaction mixture was extracted ethyl acetate and the extract was treated in a conventional manner. The residue obtained was purified by column chromatography using silica gel and elution was carried out with carbon tetrachloride-ethyl acetate (3:2). The eluate was recrystallized from ethyl acetate-hexane to give 4-(2,5-diacetoxy-3,4-dimethoxy-6-methylphenyl)-butyric acid (0.5 g) as colorless needles, melting at 125°–127° C.

Elemental analysis: Calcd. for $C_{17}H_{22}O_8$: C, 57.62; H, 6.26. Found: C, 57.59; H, 6.21.

To this product (0.323 g) was added thionyl chloride (2 ml) and the reaction was conducted at room temperature for one hour and then at 80° C. for one hour. The reaction mixture was evaporated to dryness under reduced pressure to give [6-(3-chloroformylpropyl)-2,3-dimethoxy-5-methylhydroquinone]diacetate. To a solution of this product in benzene (4 ml) was added a solution of dimethylamine (0.214 g) in benzene (1 ml) and the mixture was stirred at room temperature for 18 hours. Water was added and the mixture was extracted with ethyl acetate. The extract was treated in a conventional manner to give 6-(3-dimethylcarbamoylpropyl)-2,3-dimethoxy-5-methylhydroquinone diacetate. To a solution of this product (0.1 g) in ether (2.5 ml) was added lithium-aluminum hydride (31 mg) and with ice-cooling the mixture was stirred for 1.5 hours. Diluted hydrochloric acid was added and the reaction mixture was washed with ethyl acetate, made weakly alkaline with sodium hydrogen carbonate and extracted with ethyl acetate. The extract was treated in the conventional manner to give 2,3-dimethoxy-5-methyl-6-(4-dimethylaminobutyl)hydroquinone.

REFERENCE EXAMPLE 11

To a solution of 2,3-dimethoxy-5-methyl-1,4-benzoquinone (7 g) in chloroform was added 10% aqueous sodium hydrosulfite. After completion of reduction reaction, the chloroform layer was treated by the conventional manner to give the hydroquinone compound (6.36 g). To the solution of the product (1.84 g) in dioxane was added a mixture of 40% dimethylamine (1.2 ml) and 10% formaldehyde (3.3 ml) at 80° C. to 90° C., and the mixture was warmed for 3 hours. After 0.5 ml of the above dimethylamine and formaldehyde was further added, the mixture was warmed for additional one hour. The mixture was poured into ice water. The mixture was extracted with chloroform and the chloroform layer was treated in the usual manner to give 2,3-dimethoxy-5-methyl-6-dimethylaminomethylhydroquinone.

What is claimed is:

1. A compound of the formula

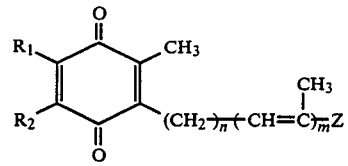

wherein $R_1$ and $R_2$ are the same or different and each is methyl or methoxy; n is an integer of 0 to 21; m is 0 or 1, and Z is morpholino methyl.

2. A compound as claimed in claim 1, wherein m is 0.

3. A compound as claimed in claim 1, wherein n is 0.

4. A compound as claimed in claim 1, wherein each of $R_1$ and $R_2$ is methoxy.

5. A compound as claimed in claim 1, wherein n is 0, m is 0 and each of $R_1$ and $R_2$ is methoxy.

6. A compound as claimed in claim 1, wherein the compound is 2,3-dimethoxy-5-methyl-6-(N-morpholino)methyl-1,4-benzoquinone.

* * * * *